United States Patent [19]

Carr et al.

[11] Patent Number: 5,460,490
[45] Date of Patent: Oct. 24, 1995

[54] MULTI-PURPOSE IRRIGATION/ASPIRATION PUMP SYSTEM

[75] Inventors: Raymond A. Carr, Clearwater Beach; David A. Cianciolo, Largo; T. Dan Moore, St. Petersburg, all of Fla.

[73] Assignee: Linvatec Corporation, Largo, Fla.

[21] Appl. No.: 246,012

[22] Filed: May 19, 1994

[51] Int. Cl.$^6$ .................................................. F04B 49/06
[52] U.S. Cl. .................... 417/44.2; 417/474; 417/477.2; 417/478; 417/479; 604/30
[58] Field of Search .......................... 417/44.2, 53, 474, 417/477.2, 478, 479; 604/30, 34, 118, 153

[56] References Cited

U.S. PATENT DOCUMENTS

| | | |
|---|---|---|
| 4,187,057 | 2/1980 | Xanthopoulos . |
| 4,493,695 | 1/1985 | Cook . |
| 4,627,833 | 12/1986 | Cook . |
| 4,713,051 | 12/1987 | Steppe et al. . |
| 4,714,464 | 12/1987 | Newton . |
| 4,755,168 | 7/1988 | Romanelli et al. . |
| 4,758,238 | 7/1988 | Sundblom et al. . |
| 4,798,580 | 1/1989 | De Meo et al. . |
| 4,832,685 | 5/1989 | Haines . |
| 4,902,277 | 2/1990 | Mathies et al. . |
| 5,006,050 | 4/1991 | Cooke et al. ........................... 417/478 |
| 5,041,096 | 8/1991 | Beuchat et al. . |
| 5,105,983 | 4/1992 | Sancoff et al. ......................... 417/478 |
| 5,106,366 | 4/1992 | Steppe .................................. 417/477.2 |
| 5,125,891 | 6/1992 | Hossain et al. . |
| 5,131,816 | 7/1992 | Brown et al. ........................... 417/478 |
| 5,195,960 | 3/1993 | Hossain et al. . |
| 5,213,483 | 5/1993 | Flaherty et al. ....................... 417/477.2 |
| 5,246,422 | 9/1993 | Favre . |
| 5,252,044 | 10/1993 | Raines et al. .......................... 417/479 |
| 5,257,917 | 11/1993 | Minarik et al. ........................ 417/477.2 |
| 5,267,956 | 12/1993 | Beuchat . |
| 5,282,787 | 2/1994 | Wortrich . |
| 5,302,093 | 4/1994 | Owens et al. . |
| 5,322,422 | 6/1994 | Natwick et al. ........................ 417/474 |
| 5,397,222 | 3/1995 | Moss et al. ............................ 417/477.2 |

OTHER PUBLICATIONS

Smith+Nephew Dyonics InteliJET Fluid Management System Tube Set Kit, Cat. #4298 Operating Room Protocol for Handling Tube Set (1 page) (Date Unk).
Anthrex Continuous Wave Arthroscopy Pump, AR–6300, Operating Instructions, 13 pages (Date Unk).
Orthoconcept Arthro FMS III, Arthroscopic Fluid Management System with Shaver Interface (2 pages) (Date Unk).
Karl Storz Endoscopy, Nezhat–Dorsey Hydro–Dissection Pump System, (publication #C431–7500–1191, 4 pages) (Date Unk).
O.R. Concepts, Inc. IrrigaTORR High Flow Irrigation System (1 page) (Date Unk).
Zimmer CDIS Controlled Distention Irrigation System, 1990 (4 pages).

(List continued on next page.)

Primary Examiner—Richard A. Bertsch
Assistant Examiner—Xuam M. Thai
Attorney, Agent, or Firm—Gene Warzecha

[57] ABSTRACT

An irrigation/aspiration pump system capable of operating in a plurality of different modes suitable for a variety of different endoscopic surgical procedures. The irrigation/aspiration pump system operates with a selected one of a plurality of tubing sets, each tubing set being adapted to provide irrigation and aspiration for a particular surgical procedure and coded to define the type of procedure for which the tubing set is designed. Each tubing set is adapted to be received by the irrigation/aspiration pump console in a way which enables the code associated with the tubing cassette to be automatically read by a code detecting means associated with the system. The code detecting means supplies appropriate control signals to different parts of the irrigation/aspiration pump system in order to assure that the parameters with which the system will be operating, when the chosen tubing set is being used, are those for which the tubing set is designed. A simplified one-piece cassette housing is utilized to retain a plurality of flexible conduits within predetermined positions relative to each other and relative to associated components of the pump system console.

21 Claims, 12 Drawing Sheets

OTHER PUBLICATIONS

Karl Storz, Pump for Instillation of Fluids, p. HYST 16, Method of operation (Date Unk).

Olympus Aqua–Purator Pump 1 page product sheet (Date Unk).

Smith+Nephew Dynonics Integrating Innovative Fluid Management with Arthroscopic Cutting Excellence, InteliJet Nov. 1992 (6 pages) (Date: Nov. 1992).

Arthrotek IES 1000 Integrated Endoscopy System, 1992 (8 pages).

Minnesota Mining and Manufacturing Company, New 3M Arthroscopy Pump, 1986 (4 pages).

Davol Inc. Arthro–Flo High Flow Irrigator, Publication #OP–AF00015000–R (4 pages) (Date Unk).

Cabot Medical, A Fully Integrated Laparoscopic Irrigation & Instrumentation System, 1991 (4 pages).

Arthrex Catalog Sheet (pp. 10–11) showing the Continuous Wave Irrigation Pump (Date Unk).

Snowden–Pencer Irrigation Pump product sheet, p. 16 (Date Unk).

United States Endoscopy Group, Inc., Ad for Pulse Laparoscopic Irrigation Systems, p. 11 (Date Unk).

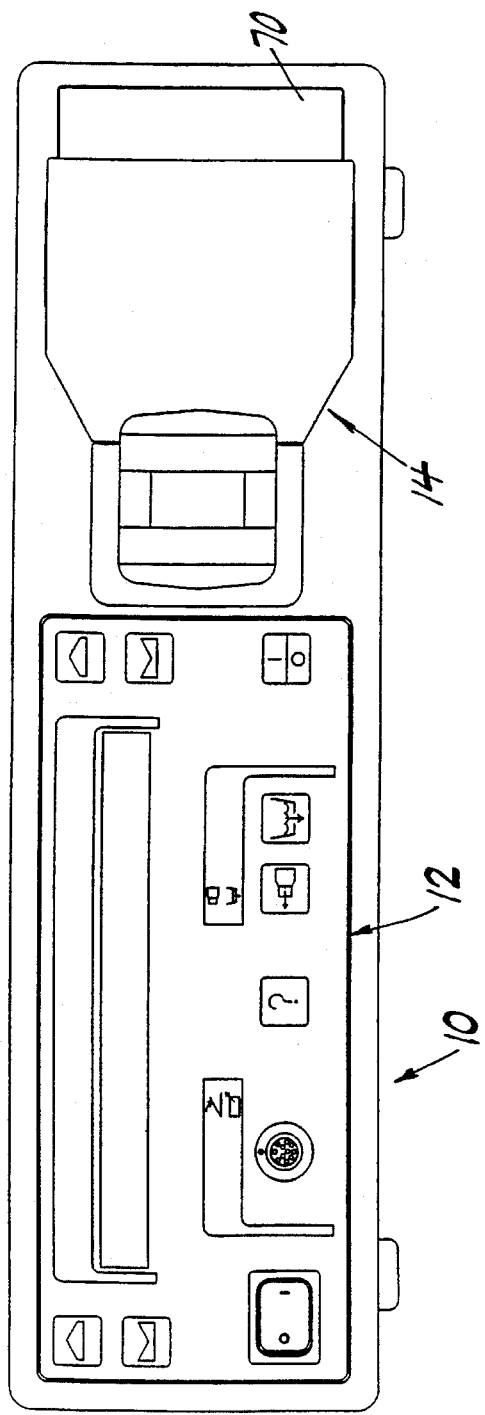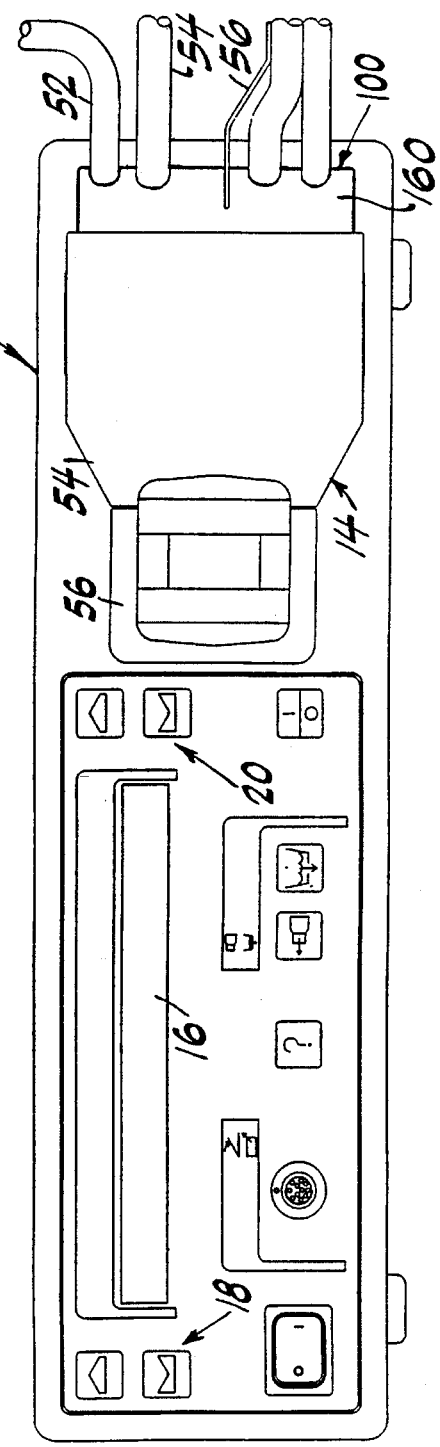

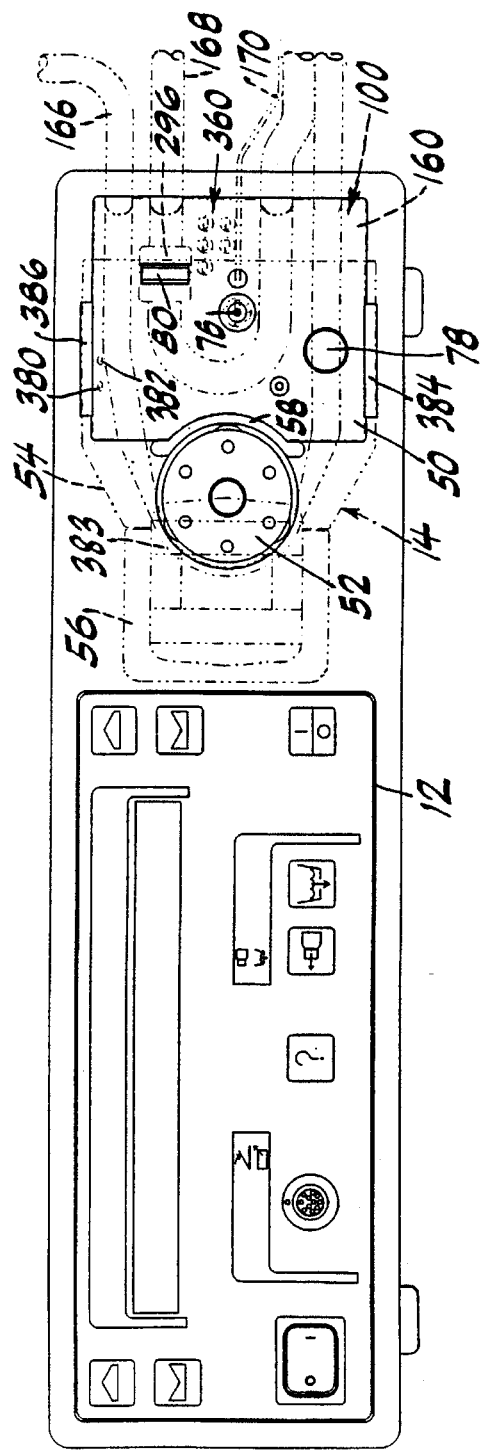
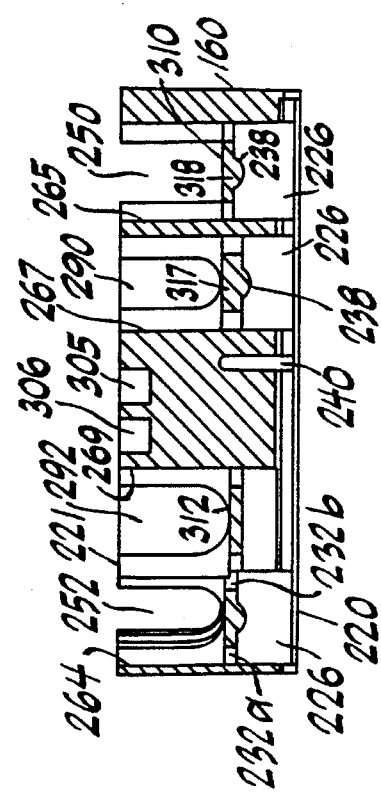
FIG. 4
FIG. 11

1

MULTI-PURPOSE IRRIGATION/ASPIRATION PUMP SYSTEM

BACKGROUND OF THE INVENTION

1. Field of the Invention

The invention relates to systems for the irrigation and/or aspiration of fluids into or from a surgical work site during an endoscopic procedure. More particularly, the invention relates to a multi-purpose irrigation/aspiration system for use during minimally invasive surgery for the purpose of performing any one of a variety of irrigation/aspiration functions such as, for example, tissue lavage, joint distension or uterine distension.

2. Description of the Prior Art

Minimally invasive surgery, also referred to herein as endoscopic surgery, often utilizes an irrigation system to force suitable biocompatible fluid into the area surrounding the surgical work site within a patient. The term "irrigation" is used broadly to mean any type of pressurized fluid flow whether it be for irrigation in particular or other uses described below. Flexible plastic tubing is used to conduct the fluid from a source to the work site and from the work site to a drain or other receptacle. Flexible tubing is also sometimes used as a pressure monitoring line to convey fluid pressure information to a control mechanism. Depending upon the procedure, the irrigating fluid is useful for various purposes such as tissue lavage, hydro-dissection, joint distension, uterine distension, etc. Known irrigation systems include electrically driven pump systems, in which a suitable fluid is pumped through flexible tubes from a source to the work site, gravity-feed systems in which the pump is replaced by merely adjusting the height of the fluid supply above the patient and nitrogen powered systems.

Known aspiration systems employ any source of reduced-pressure (i.e. lower than that of the work site) and include vacuum systems, in which a vacuum source is simply connected via flexible tubes to the work site, and simple gravity controlled drain lines. Aspiration of the fluid serves to either simply remove it to prevent undesirable accumulation or high pressure at the work site, or to regulate the flow rate to maintain a predetermined fluid pressure at the work site.

Because the irrigation and aspiration functions are commonly used together, prior art irrigation/aspiration systems have been developed to perform both functions with one system, often combined in one console. The irrigation system is generally used in conjunction with an aspiration system which removes the fluid pumped into the work site at a controlled rate depending on the flow rate selected by the surgeon. Each system utilizes a collection of flexible tubes to connect the fluid and vacuum sources to appropriate instruments inserted into the body. The collection of tubes includes a fluid inflow conduit, a fluid outflow conduit and, in some instances, a pressure monitoring conduit. All of the tubes are packaged together as a tubing set and each tubing set is produced as a unit containing all necessary tubes and connections required for performing a particular procedure with a particular system.

Some prior art irrigation/aspiration systems and tubing sets required considerable effort on the part of the operating room staff in order to hook-up the tubing set to the system and the patient. Consequently, disposable cartridges or cassette tubing sets have been developed for certain irrigation/aspiration systems.

For example, the Intelijet™ Arthroscopic Fluid Management System marketed by Dyonics utilizes a disposable tubing cassette adapted to engage and be operated by a control console. This cassette is formed of two flat mating halves which, when secured together, form a housing which contains two molded conduits, one of which contains a silicone tube. The ends of each conduit are adapted to be connected to the ends of external PVC tubes. The housing also contains an impeller which is rotated by a corresponding drive member in the console when the cassette is properly placed and, in one of the conduits, a membrane in the inflow line for use with a pressure transducer on the console. This cassette requires that at least four separate tubes be connected to their respective portals in the cassette housing.

Similar tubing cassettes are also known in ocular surgical irrigation/aspiration pumps such as described in U.S. Pat. No. 4,713,051 (Steppe et al.). This cassette is a flat housing having top and bottom mating portions which enclose an intermediate portion of an irrigation conduit and an intermediate portion of an aspiration conduit. The housing includes a pressure or vacuum sensing line and is designed to be plugged into a system console which provides power and control for irrigation and aspiration functions.

While these cassettes simplify set-up of the systems, they are somewhat complex and the systems are not single irrigation/aspiration systems capable of automatically performing more than one dedicated function. Prior art procedures often involve the use of a separate irrigation/aspiration system for a single type of endoscopic procedure because the various operating characteristics (pressure, flow rate, etc.) required of an irrigation/aspiration system intended for use with different procedures depend upon the procedure and the portion of the body involved. Thus, a hysteroscopic irrigation system is used for hysteroscopic procedures, an arthroscopic irrigation system is used for arthroscopic procedures and a laparoscopic irrigation system is used for laparoscopic procedures. Each individual procedure incorporates the use of specific tubing sets designed to work with a particular irrigation/aspiration system and to perform specific functions uniquely tailored for that procedure in order to connect the irrigation/aspiration system to the particular work site.

For hysteroscopic and arthroscopic procedures the prior art systems deliver fluid to the joint or the uterus for the purpose of controlled distension for clearing debris and improved visualization. Hysteroscopic and arthroscopic systems are commonly used with one or more cannulae to provide the functions of fluid inflow, aspiration and pressure monitoring. The output pressure is adjustable in these units and there is, therefore, some control over the use of the system. However, there is no known system which automatically adjusts the pressure limit available for use with a particular tubing set.

For laparoscopic procedures the prior art systems deliver fluid to the body cavity for the purpose of flushing blood or debris from the organ or for hydrodissection of tissue. The irrigation systems used in laparoscopic procedures are to be distinguished from insufflation systems intended for distension of the body cavity. Laparoscopic systems commonly employ a hand-held irrigation/aspiration probe which is provided with a multi-ported trumpet valve or the like to enable the user to select either irrigation or aspiration.

In the interest of optimizing use of equipment and space in operating rooms, it is desirable to have a single irrigation/aspiration system suitable for performing a variety of surgical procedures. One such system is described in U.S. Pat. No. 5,246,422 (Favre) in the form of a console which is capable of receiving any of a variety of tubing cassettes, each dedicated for a specific procedure. Each cassette houses a pair of peristaltic pumps and inflow and outflow tubes associated with the pumps. Each cassette also carries a stem extending from one side at a particular position which depends upon the procedure for which the cassette is intended. A plurality of detectors is situated on the console to detect the stem and each detector is associated with a particular program for operating the system as a function of the procedure for which the cassette is intended. This system utilizes a flat, two-sided cassette housing similar to the previously described cassettes. Furthermore, the coding device (i.e. stem) used in this system requires a different cassette housing for each type of tubing cassette. That is, the stem position of an arthroscopic cassette is physically different than that of a hysteroscopic cassette. It would be desirable to have an irrigation/aspiration system suitable for use with a variety of identically shaped tubing cassettes, each cassette coded appropriately for a particular procedure without the necessity for producing a different housing for each procedure.

Consequently, it is an object of this invention to produce an irrigation/aspiration system having a single inflow pump and a control system for operating the pump in accordance with predetermined characteristics defined for use during a selected one of several different surgical procedures.

It is also an object of this invention to produce a multi-purpose irrigation/aspiration system capable of operating with a variety of specific types of tubing sets, each set intended for use only during a particular type of surgical procedure.

It is also an object of this invention to produce a multi-purpose irrigation/aspiration system capable of operating with a variety of specific types of tubing sets which are each identified with a particular coding means associated with that tubing set type to identify the use for which the tubing set and/or the system associated therewith is intended.

It is also an object of this invention to produce a group of tubing sets designed to be capable of adapting an irrigation/aspiration system for use in a particular surgical procedure, each set within the group being tailored for and coded for a specific type of surgical procedure.

It is also an object of this invention to produce a tubing cassette for use with a multi-purpose irrigation/aspiration system wherein the cassette facilitates the engagement of the irrigation and aspiration tubing with the system.

It is also an object of this invention to produce a multi-purpose irrigation/aspiration system capable of operating with a variety of specific types of tubing sets which are each identified with a particular coding means associated with that tubing set, the coding means also containing means to automatically initiate a predetermined sequence of initiating steps during the power-on sequence of the system.

It is yet another object of this invention to produce a variety of simplified tubing cassettes for use with a multi-purpose irrigation/aspiration system, each cassette formed from a common housing and uniquely identified with a code identifying the procedure for which the cassette is intended.

SUMMARY OF THE INVENTION

These and other objects of this invention are achieved by the preferred embodiment disclosed herein which is a multi-purpose irrigation/aspiration pump system for use with a source of irrigating fluid and with a source of aspirating vacuum during an endoscopic surgical procedure at a surgical work site. The system comprises a console having a control means, a peristaltic pump, a pressure sensor and a flow rate control means. A tubing set comprising a cassette housing and a plurality of flexible conduits is used to connect the source of irrigating fluid and/or aspirating vacuum to the surgical work site. In some instances, the tubing set connects a pressure transducer to a pressure sensor in the console. The tubing set is adapted for use during a predetermined type of surgical procedure and contains a coding means which carries a code to identify the type of surgical procedure and selected predetermined fluid pressure and flow characteristics associated therewith. Decoding means is provided on the console for reading the coding means to determine the code. Retention means is provided for receiving and holding the tubing cassette and operatively engaging it and portions of the flexible conduits with the pump, the flow rate control means and the decoding means. Also provided is a control means responsive to the code and the pressure sensor for controlling the fluid pressure and flow in accordance with the predetermined characteristic identified by the code.

A further object of this invention is achieved by a tubing cassette for use with an irrigation/aspiration pump console. The tubing cassette comprises an integral housing which holds a first flexible tube for supplying irrigation fluid from a fluid source to the surgical work site and a second flexible tube for communicating a vacuum from a vacuum source to the surgical work site. A third flexible tube may also be provided for communicating pressure from a pressure transducer to a pressure sensor on the console. The cassette housing for receiving the first, second and third tubes comprises a code carrying means and respective first, second and third recess means for holding predetermined portions of the first, second and third tubes in predetermined positions relative to each other. The tubing cassette is adapted to automatically align predetermined parts of the housing, code means and tubes with associated parts of the system console.

The present invention is a universal pump system and method intended for use as a multi-purpose fluid delivery system. This irrigation pump can be used, for example, for uterine distension for hysteroscopic procedures, joint distension for arthroscopic procedures, or tissue lavage or hydrodissection for laparoscopic procedures. Three tubing sets are disclosed which are specific to the procedure to be performed. The hysteroscopic and arthroscopic tubing sets are intended to be used with other commercially available in-flow devices such as scope sheaths and cannulas which do not form a part of this invention. Similarly, the laparoscopic tubing set will be used in conjunction with most commercially available irrigation/aspiration delivery devices.

BRIEF DESCRIPTION OF THE DRAWINGS

FIG. 1 is a front elevation view of an irrigation/aspiration pump console constructed in accordance with the principles of this invention.

FIG. 2 is a view of FIG. 1 with a portion of an exemplary tubing set.

FIG. 4 is a view of FIG. 1 showing the tubing set and tubing set retention cover in phantom.

FIG. 11 is a cross-sectional view of FIG. 8 taken along the lines 11—11.

DESCRIPTION OF THE PREFERRED EMBODIMENT

Figure 3:
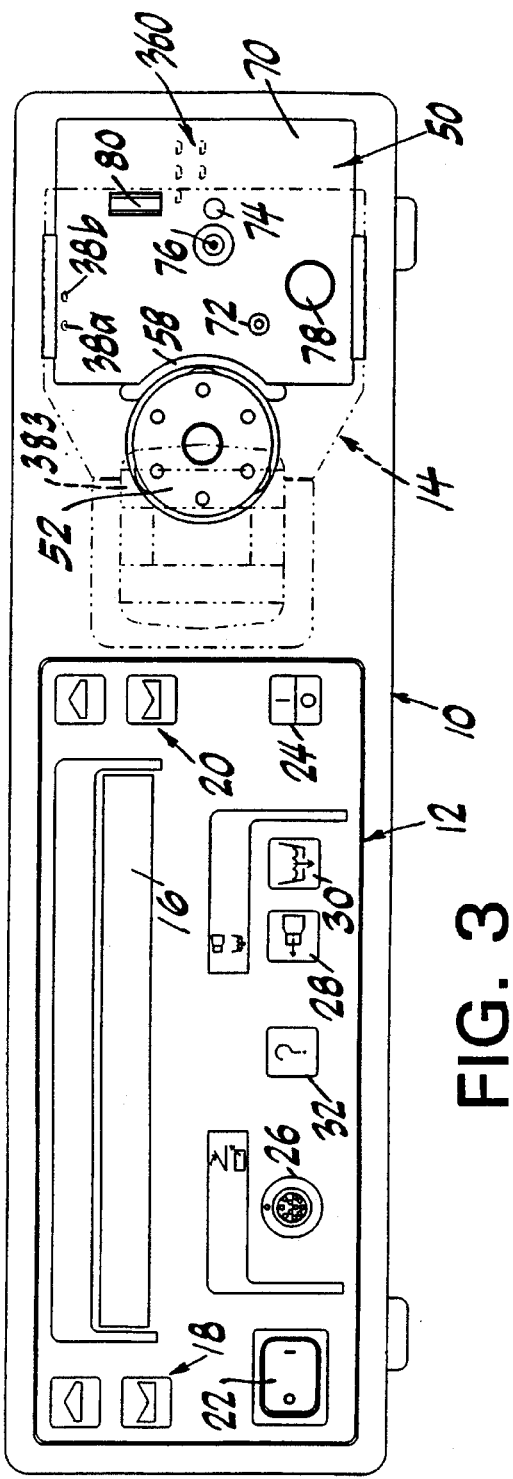
FIG. 3 is a view of FIG. 1 without the tubing set and with the tubing set retention cover in phantom.

Referring now to FIGS. 1 and 2, there is shown a front elevation view of an irrigation/aspiration pump console 10 constructed in accordance with the principles of this invention. Pump console 10 comprises a control panel 12 and a tubing cassette receiving station 14. Pump console 10 houses a peristaltic pump (best seen in FIG. 3) capable of delivering irrigating fluid from a fluid source to a surgical work site at a selected pressure and flow rate. The pump is suitable for use during a variety of selected surgical procedures and is, therefore, designed to be operable over a wide range of pressure and flow as selected on control panel display 16 by up/down pressure controls 18 and up/down flow rate controls 20. In the preferred embodiment, the pressure is selectable between approximately 0 and 30 psi (pounds per square inch) and the flow rate is selectable between approximately 0 and 2,400 ml/min (milliliters/minute). Pump console 10 is designed to operate with a tubing set and a front elevation view of pump console 10 is shown in FIG. 2 with a portion of an exemplary tubing set 100 shown in place within tubing cassette receiving station 14. FIG. 3 is a front elevation view of pump console 10 with the tubing set removed and certain portions of the tubing cassette receiving station in phantom in order to reveal certain console elements associated with the receiving station. FIG. 4 is a front elevation view of pump console 10 showing the components of FIG. 3 as well as some components of tubing set 100 in phantom in order to show the interrelationship of the various parts. FIGS. 1–4 all show the cassette receiving station 14 in a closed, ready-to-operate condition. As will be understood below, station 14 includes a cassette retention cover which is openable to enable a cassette to be placed within station 14.

Control panel 12 also includes a power switch 22, a manual aspiration flow rate control switch 24, an accessory plug connection 26 for accessories such as, for example, either a foot switch or a hand-held controller, a control switch 28 for unlocking the tubing cassette receiving station 14 and a drain control switch 30 for selecting a desired aspiration mode. Since power console 10 is microprocessor controlled and menu-driven, control panel 12 also includes a "Help" switch 32 to guide a user. Accessory plug 26 is connected to the microprocessor in such a way as to adjust the operation of the system to the particular accessory being used.

Cassette receiving station 14 comprises a cassette engaging platform 50, a peristaltic pump roller 52, a hinged cassette retention cover 54 and a cassette cover actuator 56. An arcuate guide wall 58 extends from the front of console 10 and is interposed between the peristaltic pump roller 52 and cassette platform 50 for purposes which will be understood below. Platform 50 comprises an elastomeric sheet 70 which covers an area approximately the size of a tubing cassette housing described below. Sheet 70 has a plurality of cutouts through which various console elements engage tubing set 100. For example, as will be understood below, positioning pins 72 and 74 protrude from the front of console 10 with a conical tip in order to engage corresponding bores in the rear of cassette housing 160; pressure sensing port 76 protrudes from the front of console 10 in order to engage a pressure line adapter; pressure sensor 78 is exposed through sheet 70 in order to sense the output fluid pressure in the fluid output line going to the patient; and pressure regulating bar or pinch valve 80 protrudes through sheet 70 in order to regulate the amount of vacuum in the aspiration line.

Figure 5:
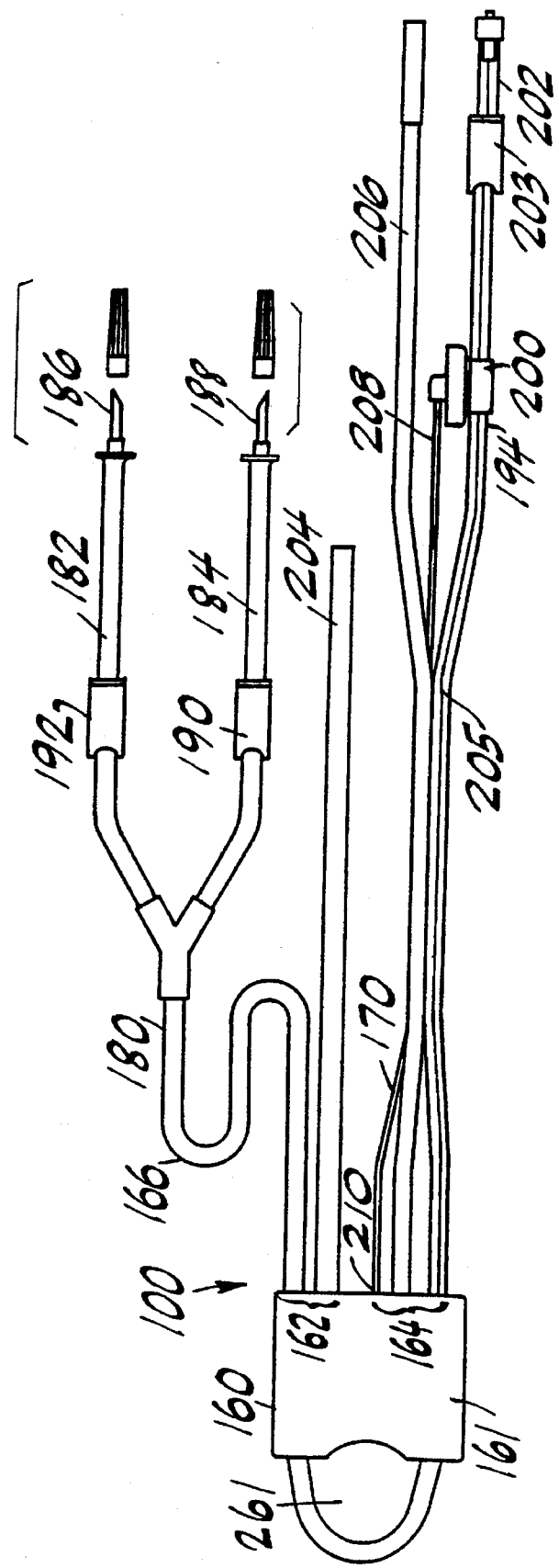
FIG. 5 is a diagrammatic view of a tubing set constructed in accordance with the principles of this invention.
Figure 6:
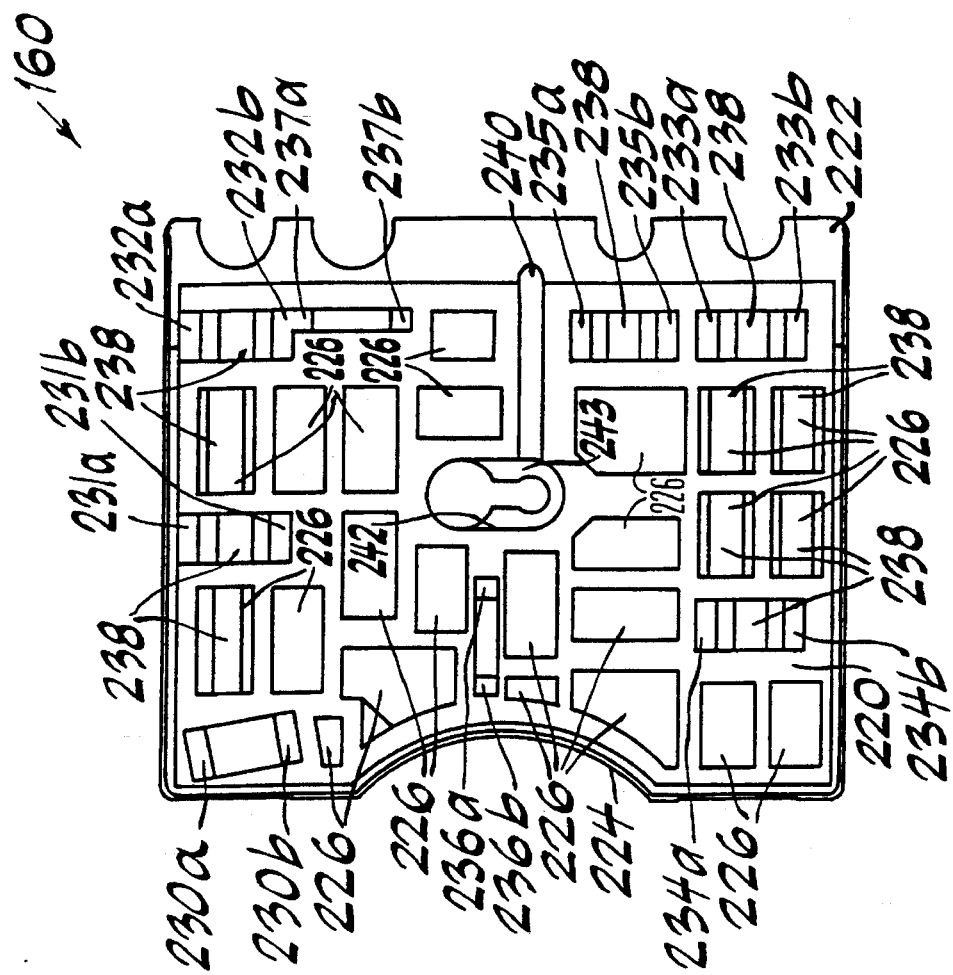
FIG. 6 is a front elevation view of the cassette housing without a cover label.
Figure 9:
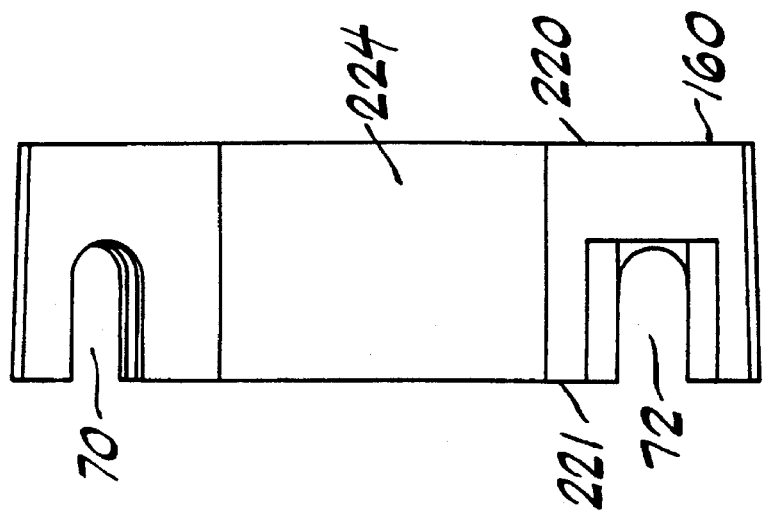
FIG. 9 is a left side view of FIG. 6.
Figure 7:
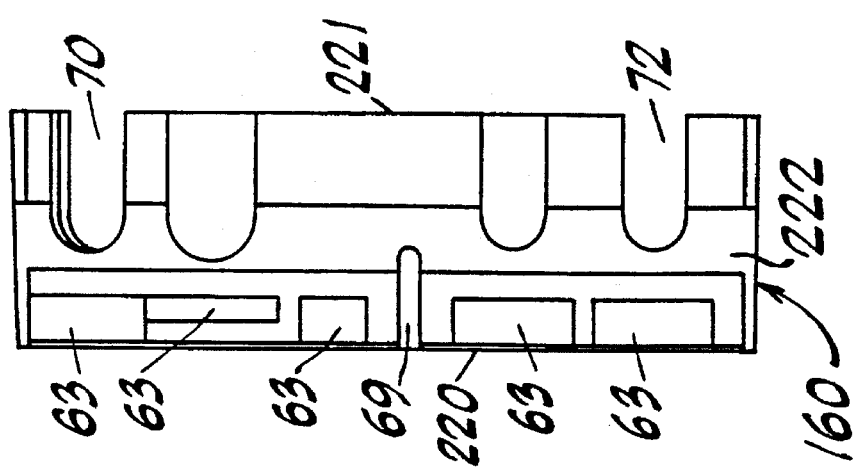
FIG. 7 is a right side view of FIG. 6.
Figure 16:
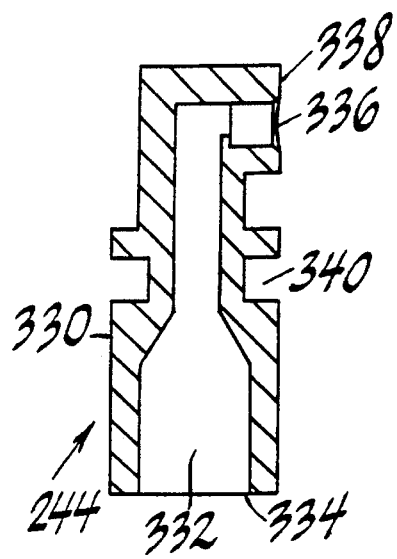
FIGS. 16 and 17 are cross-sectional elevation and right side views, respectively, of a pressure line adapter used in the invention.
Figure 17:
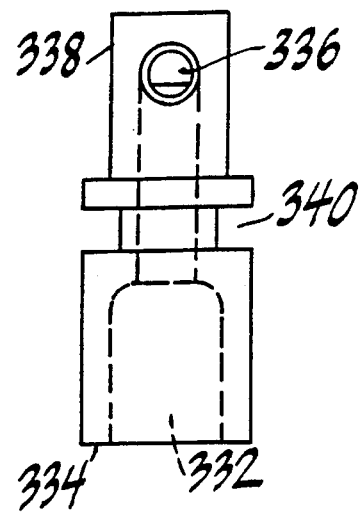
Figure 10:
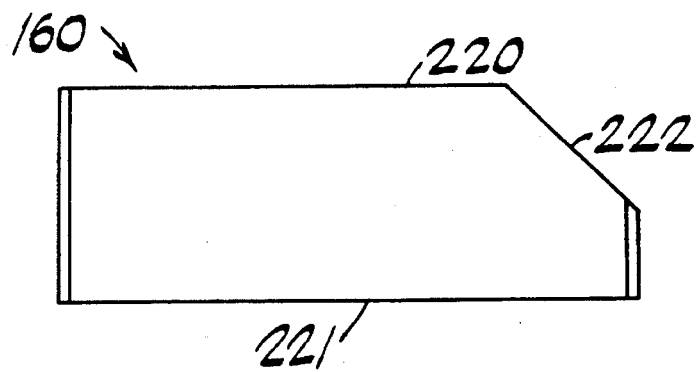
FIG. 10 is a bottom plan view of FIG. 6.

In order to better understand the system operation, it will be helpful to refer now to FIG. 5 showing the construction of a tubing set. Tubing set 100 is diagrammatically shown in FIG. 5 in the form of a "one-connection" arthroscopic tubing set (not to scale). The term "one-connection" refers to the number of irrigating fluid and pressure monitoring connections at the work site. A one-connection tubing set utilizes one fluid inflow line to supply fluid to a work site during a surgical procedure and provides pressure information to the pump console via a pressure transducer attached to the fluid inflow line. As will be understood by those skilled in the art, in arthroscopic procedures, one-connection systems are used with a simplified inflow cannula or scope sheath. A "two-connection" tubing set (briefly described in FIGS. 16 and 17) could also be used without adversely affecting operation of the system. However, two ports of an inflow cannula or scope sheath would need to be provided to enable a fluid inflow line and a separate pressure monitoring line to be connected at the work site. A two-connection tubing set provides a way to determine pressure at the work site while a one-connection tubing set determines pressure at a given point in the fluid path.

Tubing set 100 comprises a plurality of elongated flexible conduits (such as PVC tubes) which are retained within a housing cassette 160 situated at a point intermediate the ends of the tubes. As in some prior art systems, tubing cassette housing 160 of the present invention facilitates the set up of the equipment in preparation for a surgical procedure by enabling a plurality of connections to be made with only one step—that of placing the cassette into position in the receiving station. Tubing set 100 is representative of a disposable tubing set usable with pump console 10. Each tubing set associated with a particular procedure could have a differently colored cassette 160 or cassette label 161 and each separate tube within each cassette could be identified by different colors or markings to facilitate hooking up the system to the patient and fluid supplies. The different colors or other indicia could indicate that the system is programmed to automatically limit flow and pressure ranges depending upon the procedure and the tubing set. Since tubing set 100 is interposed between a patient and sources of fluid and vacuum and since cassette housing 160 is connected intermediate the ends of the tube, the input and output of cassette 160 may be referred to as a supply side 162 and a patient side 164.

The tubes retained by cassette 160 comprise an irrigation conduit 166, an aspiration conduit 168 and a pressure sensing conduit 170. Irrigation conduit 166 is conventional and is provided at its supply end 180 with two legs 182 and 184, each having a spike tip 186 and 188, respectively, for penetrating an irrigating fluid pouch (not shown) and a pair of clamps 190 and 192. The fluid source may be any suitable low viscosity fluid such as dextrose in water, saline and glycine sorbitol, etc. Irrigation conduit 166 passes from supply end 180 through cassette housing 160 to delivery or patient end 194. Depending upon the particular tubing set and/or procedure to be performed, the connections between the delivery end 194 and the work site may vary. However, for the arthroscopic, one-connection tubing set shown, tube end 194 is connected to a pressure transducer 200 which is provided with an extension tube 202 having a clamp 203 and suitable conventional connectors for attaching irrigation conduit 166 to cannulae or instruments at a surgical work site. The patient side irrigation tubes 194 and 202 are shown with a longitudinal stripe 205. As will be understood below, cassette 160 assures the placement of an intermediate portion of irrigation conduit 166 adjacent a peristaltic pump in order to pump fluid from the supply to the patient.

Aspiration conduit 168 has a source end 204 adapted for connection to a source of vacuum which may be, for example, a conventional vacuum fitting in the wall of an operating room (or in a drain canister which is in turn connected to the vacuum source) and a patient end 206 adapted to be connected to a cannulae or instruments to withdraw fluid from a surgical work site. As will be understood below, aspiration conduit 168 is held, by cassette housing 160, adjacent pressure regulating bar 80 which regulates the aspiration flow rate according to the value set on the control panel.

The diameters of conduits 166 and 168 may vary from supply side 162 to patient side 164. In the preferred embodiment, the diameter and the wall thickness of the fluid supply line between the fluid supply and the cassette are greater than the diameter and wall thickness of the fluid supply line between cassette 160 and the patient. This enhances the operation of the system and strengthens the tubes to make them more durable. Similarly, the diameter and thickness of the aspiration line between the vacuum source and the cassette are greater than that between the cassette and the patient. This also minimizes any damage to the source-side tubing during a procedure.

Since a pressure transducer 200 is utilized in certain procedures to sense the fluid supply pressure at a predetermined point in the fluid flow path, the invention includes a means to securely connect the transducer to conical port 76 on console 10. Port 76 is connected to an air pressure sensor (not shown) within the control panel and is used during operation of pump console 10 in order to regulate rollers 52 to control the output pressure of the system. In the preferred embodiment, pressure monitoring line 170 has a transducer end 208 adapted to connect pressure line 170 with a suitable pressure transducer 200 (best seen in FIG. 15) and a cassette end 210 adapted to be connected to cassette 160 as will be explained below.

Figure 12:
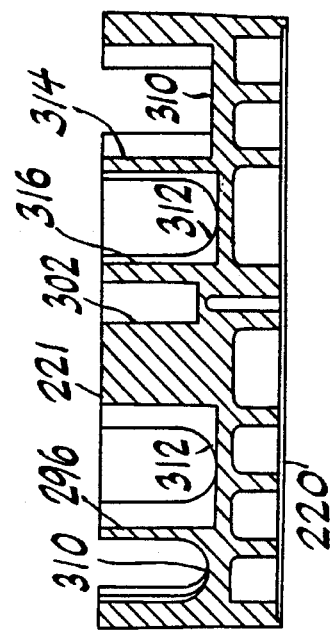
FIG. 12 is a cross-sectional view of FIG. 8 taken along the lines 12—12.
Figure 13:
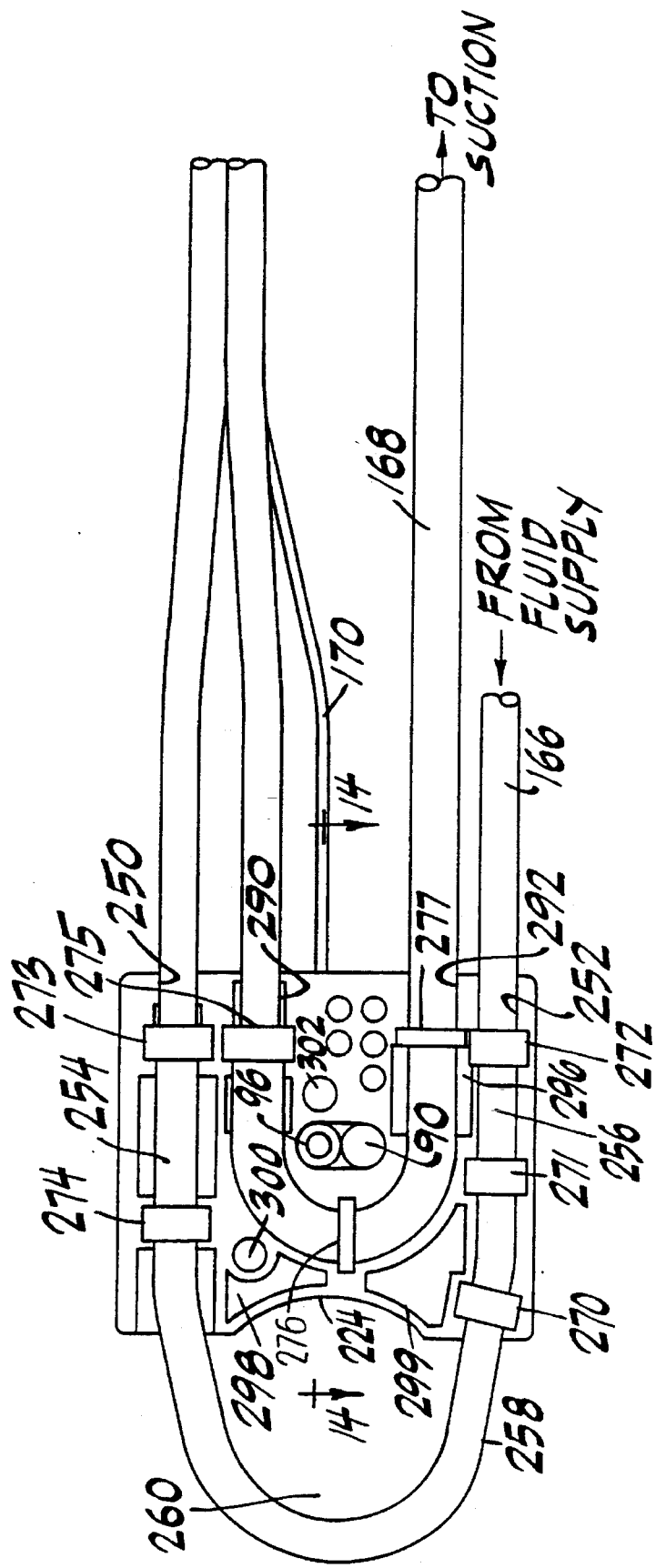
FIG. 13 is a diagrammatic view of a portion of the tubing set of FIG. 5 showing the rear surface of the cassette housing in relation to the tubing retained thereby.

The structure of cassette housing 160 may best be seen in FIGS. 6 through 12 and the relationship between cassette 160 and the flexible tubes of the tubing set may best be seen in FIG. 13. It will be noted that cassette 160 facilitates engagement of the tubing set with console 10 by enabling both the inflow and outflow tubes to be turned back upon themselves, thereby entering and exiting housing 160 on one edge. Cassette housing 160 is an integrally molded plastic body having a front surface 220 adjoining on one side in an inclined surface 222 and on the other side in an arcuate, guide wall engaging surface 224. The guide wall engaging surface 224 engages the convex side of arcuate guide wall 58 when the cassette is placed into receiving station 14. Front surface 220 has a plurality of material relief recesses 226 in several locations across its entirety and a plurality of parallel, spaced clip-receiving aperture or slot pairs 230a and b, 231a and b, 232a and b, 233a and b, 234a and b, 235a and b, 236a and b and 237a and b. The aperture pairs are adapted to receive and hold tube-retaining clips, as will be understood below. Certain ones of the recesses 226 contain raised ribs 238 (best seen in FIG. 11) which facilitate material flow in the molding process. A pressure sensing conduit channel 240 is provided between inclined surface 222 and oblong pressure sensor adapter aperture 242 to receive end 210 of pressure sensing conduit 170. Pressure sensor adapter aperture 242 extends between front and rear cassette surfaces 220 and 221 and includes a C-shaped rib 243 parallel to the front and rear cassette surfaces approximately midway between them. The rib is adapted to receive a pressure line adapter 244 as will be further explained below. Substantially all of the detail shown in FIG. 6 can be covered up by a label as best seen in FIG. 5.

Figure 8:
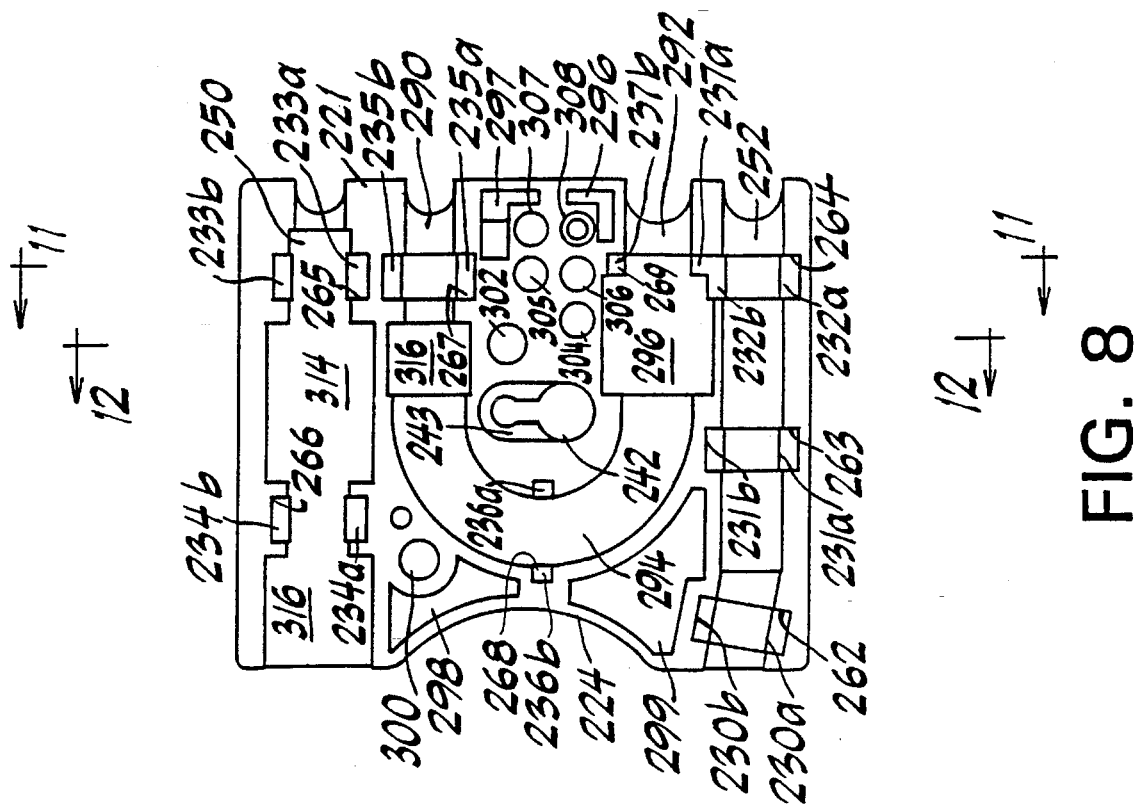
FIG. 8 is a rear elevation view of FIG. 6.

Cassette rear surface 221, best seen in FIG. 8, is provided with a plurality of tubing channels intended to maintain the various tubing set conduits in a predetermined orientation relative to each other in order to enable them to be situated adjacent the front of pump console 10 in a particular orientation so as to be engaged by various components to be described. Thus, as best seen in FIGS. 8 and 13, rear surface 221 comprises fluid inflow channel having a pair of generally parallel fluid supply channel sections 250 and 252 for receiving and holding predetermined tubular portions 254 and 256 of fluid supply tube 166 fixed relative to each other in order to form a semi-circular loop 258. Loop 258 and guide wall engaging surface 224 define an enclosed pump roller receiving space 260 adapted to engage the peristaltic roller head 52. (During shipment of tubing set 100, roller receiving space 260 may be filled with a foam insert 261 as best seen in FIG. 5.) Rear surface 221 also comprises a fluid outflow channel having a pair of parallel channel sections 290 and 292 joined by an arcuate channel section 294 for holding aspiration line 168 in a predetermined position. Channel 292 is provided with an enlarged area 296 which enables the aspiration line 168 to be engaged by regulating bar 80 extending through cassette sheet 70 as will be understood below.

Figure 20:
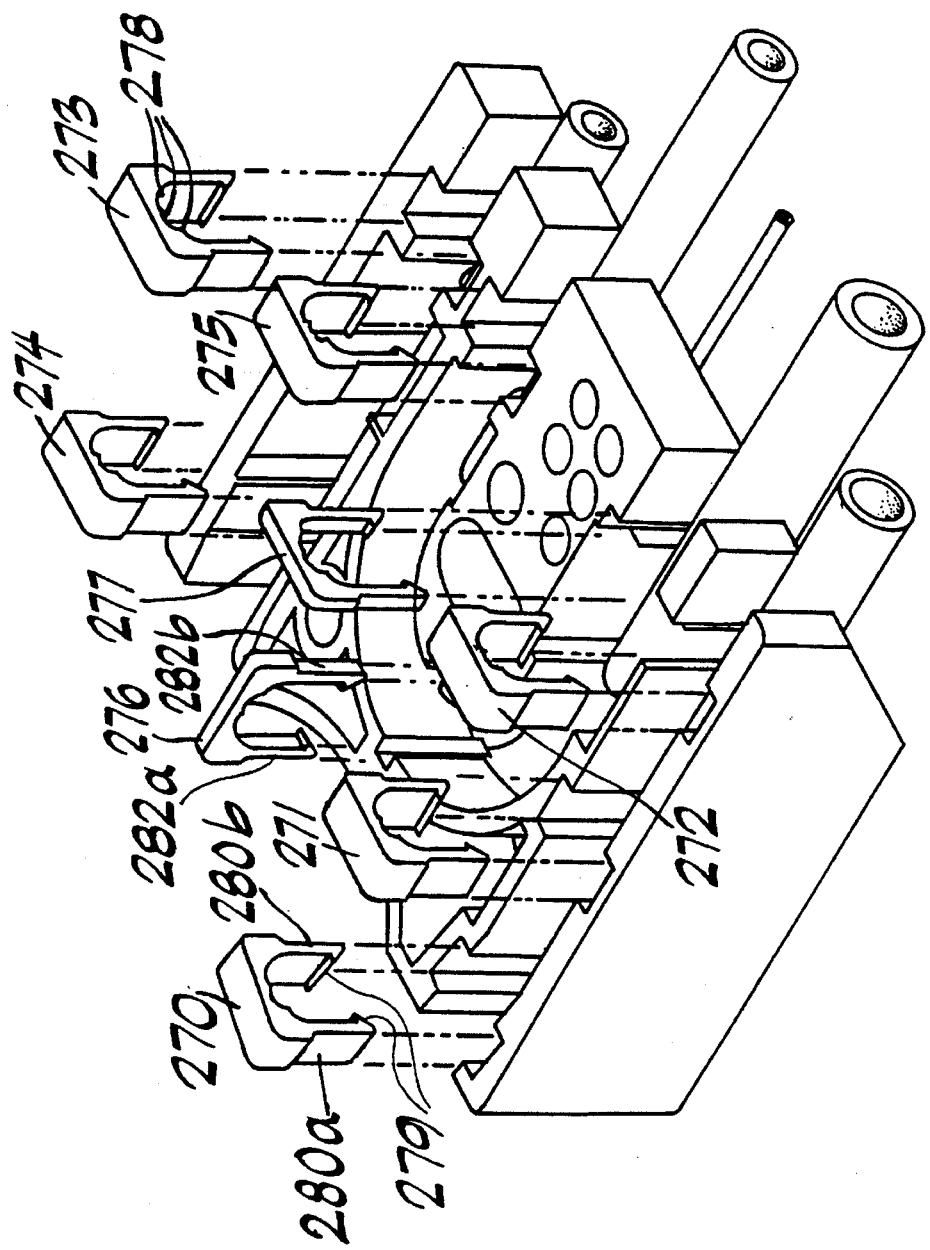
FIG. 20 is an exploded perspective view of the rear surface of the cassette housing of the tubing set.

Rectangular clip-receiving channels 262, 263, 264, 265, 266, 267, 268 and 269 are longitudinally spaced along channel sections 250, 252 and 290, 292 and 294, and are aligned with associated slot or aperture pairs 231a and b through 237a and b, respectively. Each slot pair is transversely spaced relative to its associated channel. As best seen in FIGS. 13 and 20, large clips 270–275 and small clips 276 and 277 are provided to be received within channels 262–267, respectively. The interior surface of each clip is generally U-shaped with the base of the "U" having three parallel pointed ribs 278 projecting radially inwardly. Both legs of each clip have opposing, inwardly directed retaining ledges 279. Each clip 270–277 is inserted from the rear into a corresponding channel over a tube such that the clip legs 280a and b, and 282a and b are pushed into and through apertures 230a and b, etc. and snap over the aperture edge to the front side of cassette 160. The clip-receiving channels and clips are spaced along the irrigation conduit 166 as well as the aspiration conduit 168. Clip-receiving channels 262–267 and corresponding clips 270–275 are wider than channels 268,269 and clips 276, 277 in order to facilitate assembly of the tubing in the cassette since the preferred embodiment employs different diameter tubes. Some adhesive may also be used to secure the tubes to the cassette, preferably in the area of clips 270, 271 and 272 to relieve pulling strain on these clips during rotation of roller 52.

Cassette rear surface 221 is provided with material relief recesses 296–299 and positioning apertures 300 and 302 in order to engage positioning pins 72 and 74, respectively, to facilitate proper placement of cassette 160 in receiving station 14. A plurality of code receiving apertures 304, 305, 306, 307, 308 are provided to retain one or more selected code carrying devices in order to identify a particular cassette as being designed to be used with a particular type of surgical procedure. In the preferred embodiment a magnet is placed in one or more apertures 304–308 and the particular pattern of magnets defines the code.

Generally, as best seen in FIGS. 11 and 12, the bottom surface 310 of irrigating fluid channels 250, 252 and the bottom surface 312 of aspirating fluid channels 290, 292, 294 are rounded to conform to the tubes to be received in the channels. However, the shape of these bottom surfaces is flat in the areas of the clip-receiving channels, as well as at regulator bar area 296, pressure monitor area 314 and expansion area 316. Additionally, tube coupling area 316 has a flat bottom surface to accommodate a coupling between two different size aspiration tubes. In order to facilitate manufacture and assembly, all of the clips 270–277 may have the same leg length and internal radius of curvature. To assure a secure fit between the clips and tubes of varying diameters, any slack between the ribs 278, bottom surfaces 310, 312 and the tubes may be taken up by varying the thickness of the channel bottom. This is best seen in FIG. 11 by reference to the difference in thickness between wall 317 and 318.

Figure 14:
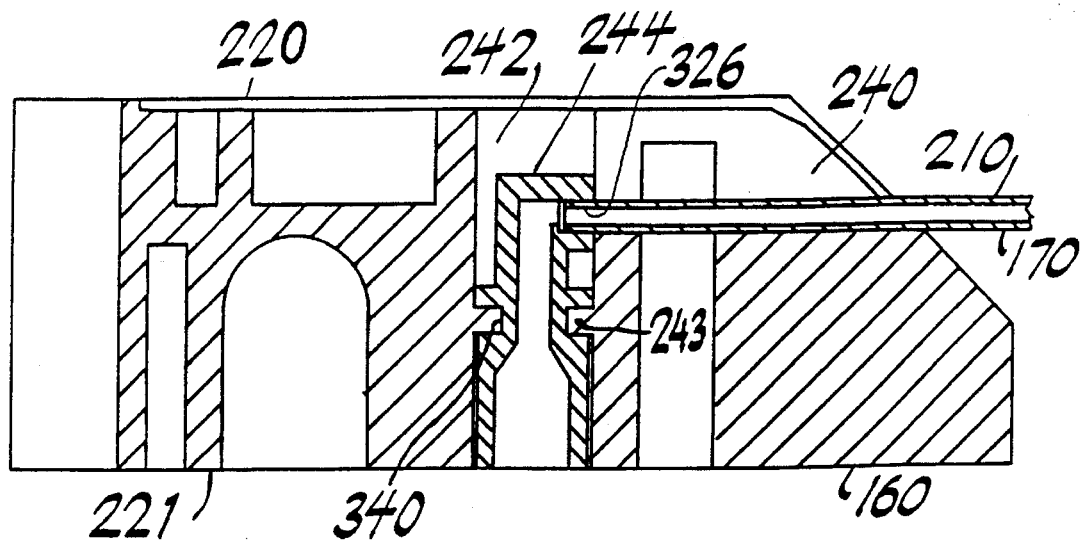
FIG. 14 is a cross-sectional view of FIG. 13 along the lines 14—14.
Figure 15:
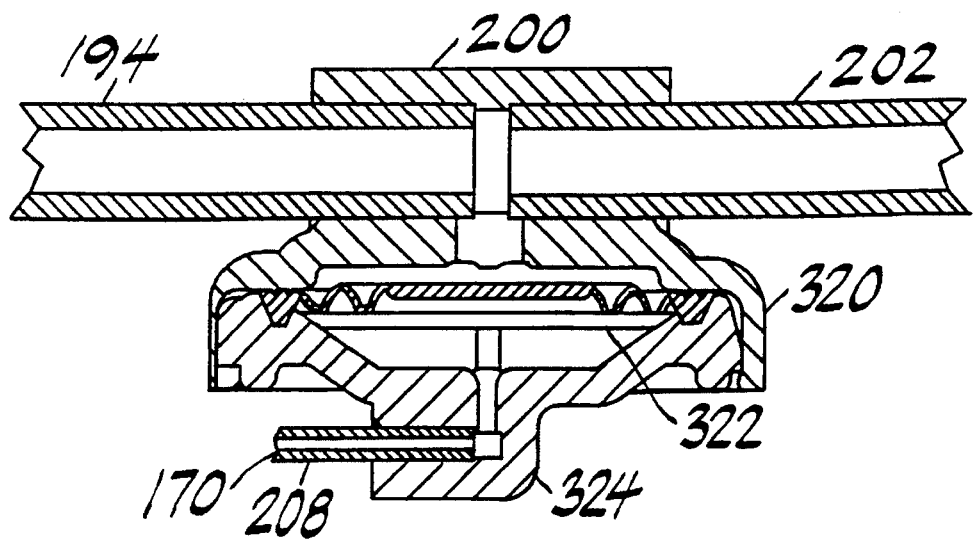
FIG. 15 is an exploded and inverted view of the pressure transducer shown in FIG. 5.

Pressure transducer 200 and its connection to cassette 160 will now be described by reference to FIGS. 5, 14 and 15. FIG. 15 shows an exploded (and inverted) cross-sectional view of transducer 200 which is shown diagrammatically in FIG. 5 in relation to other components of tubing set 100. Transducer 200 comprises a housing 320 containing irrigating supply line 194 and extension 202, diaphragm 322 and cover 324. The latter retains end 208 of pressure sensing line 170. The other end 210 of line 170 is connected to a port of adapter 244, shown in FIG. 14. Adapter 244 (best seen in FIGS. 14, 16 and 17) has a generally cylindrical hollow pliable body 330 having a hollow interior 332 open to ambient at one end 334 of body 330 and open to a laterally directed pressure line port 336 at the other end 338 of body 330. Adapter 244 has an annular channel 340 adapted to engage rib 243 and hold body 330 in a fixed position. One end of pressure line 170 is connected to port 336 and end 334 is held, as will be understood below, against pressure sensor port 76. It will be understood that, during assembly, adapter 244 is inserted into the large end of aperture 242 and then moved into alignment with channel 240. The pliable nature of body 330 and end 334 helps to establish a secure, releasable connection between the pressure line and internal pressure sensor.

Figure 19:
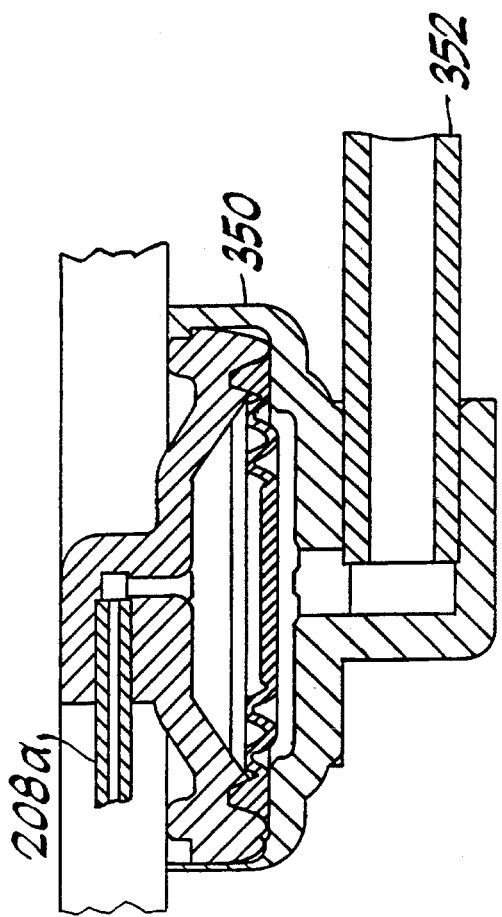
FIG. 19 is an exploded and rotated view of the pressure transducer shown in FIG. 18.
Figure 18:
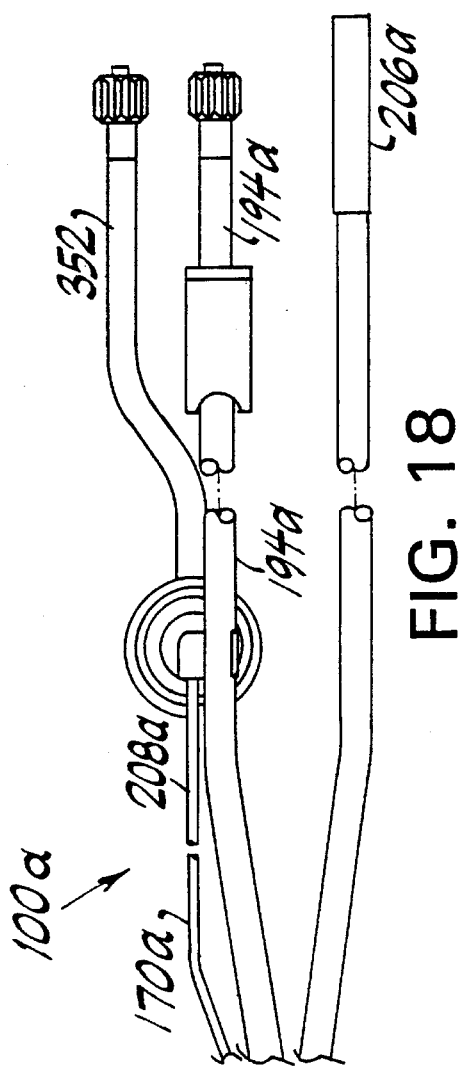
FIG. 18 is a diagrammatic view of the patient end of an alternate embodiment of a tubing set.

An alternate embodiment of pressure transducer 200 is shown in FIGS. 18 and 19. FIG. 18 shows the patient ends of a two-connection tubing set 100a, the remaining unshown components being identical to corresponding elements of tubing set 100. Tubing set 100a utilizes a suction line 206a, identical to conduit 206, and a supply line 194a which, unlike conduit 194 which ends at transducer 200, is unbroken and continues onto the surgical work site. In the two-connection tubing set 100a, there is a transducer 350 interposed between end 208a of pressure conduit 170a and a pressure monitoring conduit 352, the distal end of which is adapted to engage a suitable point adjacent the surgical work site for providing pressure information.

While pressure transducers 200 or 350 provide pressure information for dynamic control of pump roller 52, a separate pressure sensor 78 is provided on console 10 for use with tubing sets which are not adapted to sense pressure at the work site. Pressure sensor 78 may be used not only to control the pump but also as a back-up to transducer 200/350 to detect any undesirable increase in pressure in irrigation conduit 166. This sensor can trigger a signal to stop the pump in the event of a sudden or undesirable pressure increase. Sensor 78 may comprise an elastomeric membrane or piston extending from the front of console 10 and adapted to be held (by cassette 160) in direct contact with the fluid supply conduit.

Referring now to FIGS. 3 and 4, console 10 is provided with code detecting means 360 to detect the code associated with a given cassette housing and to provide appropriate control signals to a microprocessor controller within console 10 to achieve the required parameters defined by the code. In the preferred embodiment, code detecting means 360 comprises a plurality of magnetically responsive switches (shown diagrammatically in phantom behind elastomeric sheet 70) arranged in a pattern so as to have each switch be situated adjacent a corresponding magnet in apertures 304–308 (also shown in phantom in FIG. 4) at the rear of cassette 160. If other code carrying elements are used (e.g. optical, mechanical, etc.) appropriate sensors must also be used. Additionally, retention cover status sensors 380 and 382 cooperate with a magnet set in a hook extension (not shown) of cover 54 to determine whether it is open, closed or locked. The retention cover covering the cassette must apply sufficient pressure to ensure proper operation including secure connection of the pressure adapter with the pressure sensing port. All pumping action ceases when the door is not locked. In the preferred embodiment, cover 54 opens outwardly about hinge 383 to receive cassette 160 and a pair of slots 384 and 386 in the front of console 10 are adapted to receive hook-shaped extensions (not shown) of cover 54 when the cover is closed. When the top extension is detected by sensor 380, a motor (not shown) is automatically activated to move the cassette cover to the right (as seen in FIG. 4) in order to engage each hook-shaped extension with an associated cam surface at the right side of each slot 384 and 386 to press cover 54 and cassette 160 against platform 50. When the cover moves sufficiently to have the magnet in the extension detected by sensor 382, the cover is then in the "locked" position. Once sensor 382 verifies the locked position, the code located on the cassette is scanned and interpreted and an initiating sequence is begun. If a valid code is identified, then the system is enabled.

The coding means associated with each cassette housing identifies a predetermined operational characteristic associated with the irrigation/aspiration system. In the preferred embodiment, these irrigation/aspiration operational characteristics are the minimum and maximum operational pressures and flow rates associated with the tubing set designed for each particular surgical procedure. The pressure parameters are generally associated with the irrigation or pumping side of the system while the flow parameters are generally associated with the regulating bar side of the system. While different tubing materials or sizes may be employed in the various tubing sets, the system can perform with the various tubing sets all having identical tube materials and sizes, provided the coding is changed to adjust the various pressure values and flow rates. Whether or not the actual material and/or size of the irrigation, aspiration or pressure conduits in each tubing set is different, the operational pressure and flow rate limits suitable for each procedure vary. Thus, the code associated with a tubing set must be able to define the limits of operational pressure and flow rates. With respect to the parameters associated with arthroscopic, laparoscopic and hysteroscopic procedures, the following operational limits are used in the tubing sets of the preferred embodiment:

OPERATIONAL LIMITS FOR TUBING SETS IN ARTHROSCOPIC PROCEDURES

Maximum operational pressure: 150 mm Hg
Minimum operational pressure: 0 mm Hg
Maximum operational flow rate: 2400 ml/min.
Minimum operational flow rate: 0 ml/min.

OPERATIONAL LIMITS FOR TUBING SETS IN LAPAROSCOPIC PROCEDURES

Maximum operational pressure: 1000 mm Hg
Minimum operational pressure: 0 mm Hg
Maximum operational flow rate: 2400 ml/min.
Minimum operational flow rate: 0 ml/min.

OPERATIONAL LIMITS FOR TUBING SETS IN HYSTEROSCOPIC PROCEDURES

Maximum operational pressure: 300 mm Hg
Minimum operational pressure: 0 mm Hg
Maximum operational flow rate: 750 ml/min.
Minimum operational flow rate: 0 ml/min.

Thus, when used in conjunction with the associated procedural cassette and tubing set, the universal pump system will provide the low pressure variable flow needs of arthroscopy and hysteroscopy for joint or uterine distension, in addition to the variable pressure, high flow needs of laparoscopy for tissue lavage or hydrodissection.

It will be understood that other surgical procedures could be defined and suitable pressure and flow rates could be identified for tubing sets to be used with these other procedures. Additionally, other characteristics besides pressure and flow rate may be selected to be controlled by the coding means. For example, certain procedures or tubing sets may be designed to permit only remote control operation of the irrigation/aspiration pump console, a limitation on the time required to change the system from operating at the minimum operational characteristics to maximum, etc.

The system operation is menu-driven during the cassette loading and unloading procedure, the menu being controlled by a microprocessor within console 10. Menu prompts such as "OPEN DOOR" and "INSERT CASSETTE" are displayed on display 16 when the system is turned on and no cassette is detected in place. When a cassette is inserted and sensors 380 and 382 are activated, a sequence of initiating events is automatically started. For example, the "WRAP TUBING" mode is activated to assure proper seating of the tubing on roller 52. Examples of other prompts which may be desired are "CLOSE DOOR", "UNLOAD", "OPEN DOOR", "REMOVE CASSETTE", etc.

The universal pump will operate in a stand alone mode or, via a communications bus, in conjunction with an associated drive console for cutting instruments. The drive console may be a rotatable shaver system which resects tissue and/or bone during arthroscopic or other endoscopic procedure. The communications between the pump and the drive console will allow the pump to provide maximum flow rates during operation of the shaver system.

It will be understood by those skilled in the art that numerous improvements and modifications may be made to the preferred embodiment of the invention disclosed herein without departing from the spirit and scope thereof.

What is claimed is:

1. A multi-purpose irrigation/aspiration pump system for use with a source of irrigating fluid and with a source of aspirating vacuum during an endoscopic surgical procedure at a surgical work site comprising:

an elongated fluid inflow conduit connected between said fluid source and the work site;

an elongated fluid outflow conduit connected between the work site and said vacuum source;

pressure producing means for producing a predetermined fluid pressure in said fluid inflow conduit;

aspiration regulating means for regulating the fluid flow in said fluid outflow line;

pressure sensing means for sensing the fluid pressure at a predetermined point in the flow path of said fluid;

control means responsive to said pressure sensing means for controlling said pressure producing means and said aspiration regulating means;

a tubing cassette housing means comprising:

an integrally formed planar body having a front surface and a back surface, a first channel formed in and parallel to said back surface for holding a predetermined intermediate portion of said fluid inflow conduit and a second channel formed in and parallel to said back surface for holding a predetermined intermediate portion of said fluid outflow conduit, said first and second channels being open on said back surface to enable direct access of said pressure producing means and said aspiration regulating means to said predetermined intermediate portions of said fluid inflow and outflow conduits;

coding means on said cassette housing means for containing a code which identifies at least one predetermined irrigation/aspiration operational characteristic;

decoding means for determining said code contained in said coding means and communicating same to said control means;

retention means for receiving said cassette housing means and operatively engaging said fluid inflow conduit with said pressure producing means and said fluid outflow conduit with said aspiration regulating means.

2. An irrigation/aspiration pump system according to claim 1 wherein said predetermined intermediate portions of said fluid inflow and outflow conduits are retained by said housing in the form of substantially semi-circular loops.

3. An irrigation/aspiration pump system according to claim 1 wherein said pressure producing means is a peristaltic pump and said aspiration regulating means is a pinch valve, further comprising means to enable said pump and said pinch valve to directly engage said intermediate portions of said fluid inflow and outflow conduits, respectively.

4. An irrigation/aspiration pump system according to claim 1 further comprising:
  a console for containing and holding said pressure producing means and said aspiration regulating means in predetermined relative positions;
  a tubing cassette receiving means on said console for holding said tubing cassette housing means fixed relative to said pump and said pinch valve, said tubing cassette receiving means comprising:
  alignment pin means for aligning said tubing cassette housing means relative to said console;
  a hinged cover movable from a first, open position, enabling said tubing cassette housing means to be positioned on said alignment pin means, to a second, closed position in which a predetermined portion of said tubing cassette housing will be covered by said cover;
  switch means for sensing when said hinged cover is in said second, closed position;
  motor means responsive to said switch means for automatically moving said hinged cover laterally relative to said tubing cassette housing means from said second, closed position to a third, closed position;
  cam means for gradually increasing the pressure with which said cover contacts said tubing cassette housing means as said cover moves from said second, closed position to said third, closed position.

5. A tubing set for use with an irrigation/aspiration console comprising:
  a first flexible tube for supplying irrigation fluid from a fluid source to a first predetermined location;
  a second flexible tube for communicating a reduced, aspirating pressure from a source of reduced pressure to a second predetermined location;
  a flat housing for receiving predetermined intermediate portions of said first and second tubes therein, said housing having parallel front and back surfaces and comprising respective first and second channel means in said back surface for holding said predetermined intermediate portions of said first and second tubes in predetermined positions relative to each other, said first channel means comprising a pair of laterally spaced first channel sections extending entirely across said back surface and adapted to hold said first tube therein with a portion thereof extending beyond the periphery of said housing, said second channel means comprising a semi-circular second channel section, the ends of which are laterally spaced from each other and disposed parallel to and inwardly of said spaced first channel sections.

6. A tubing set according to claim 5 wherein said portion of said first tube extending beyond the periphery of said housing has a semi-circular loop shape in the plane of said housing and is adapted to engage the rollers of a peristaltic pump, the axis of which extends perpendicularly to the plane of said housing.

7. A tubing set according to claim 5 wherein said irrigation/aspiration console further comprises a pressure sensing means, further comprising:
  a third flexible tube having a first end attached to a pressure transducer and a second end, said third tube for communicating pressure from the pressure transducer to said pressure sensing means;
  tube receiving means in said housing for receiving said second end of said third tube therein and holding it in a predetermined position relative to said pressure sensing means.

8. A tubing set according to claim 7 further comprising:
  a cylindrical, hollow, flexible pressure line adapter means for being secured to said housing and for being interposed between said second end of said third tube and said pressure sensing means, said adapter closed at one end and having a first transversely directed bore adjacent said one end for engaging said second end of said third tube, said bore communicating with the interior of said adapter;
  an adapter receiving means on said housing for receiving and holding said adapter in pressure communicating contact with said pressure sensing means.

9. A tubing set according to claim 5 wherein a predetermined portion of said first and/or second tubes is adhesively retained within said first and/or second channel means, respectively.

10. A tubing set according to claim 5 further comprising:
  coding means for identifying at least one predetermined operating characteristic associated with said first and second tubes.

11. A tubing set according to claim 10 wherein said coding means is magnetic.

12. A tubing set according to claim 10 wherein said coding means is optical.

13. A tubing set according to claim 10 wherein said coding means is mechanical.

14. A tubing set according to claim 10 wherein said operating characteristic relates to the maximum pressure at which said first and/or second tubes may operate.

15. A tubing set according to claim 10 wherein said operating characteristic relates to the maximum flow rate at which said first and/or second tubes may operate.

16. A tubing set according to claim 10 wherein said operating characteristic relates to the internal diameter of said first and/or second tubes.

17. A tubing cassette housing for use with an irrigation/aspiration system in which a first flexible tube is utilized to communicate between a first source and a first work site and a second flexible tube is utilized to communicate between a second source and a second work site, said cassette housing comprising:
  a flat, integrally formed housing for receiving predetermined intermediate portions of said first and second tubes therein, said housing having parallel front and back surfaces and comprising respective first and second channel means in said back surface for holding said predetermined intermediate portions of said first and second tubes in predetermined positions relative to each other, said first channel means comprising a pair of laterally spaced first channel sections extending entirely across said back surface and adapted to hold said first tube therein with a portion thereof extending beyond the periphery of said housing, said second channel means comprising a semi-circular second channel section, the ends of which are laterally spaced from each other and disposed parallel to and inwardly of said spaced first channel sections.

18. A tubing cassette according to claim 17 further comprising:
  a plurality of transversely spaced slot pairs longitudinally spaced along said first and second channels;

a plurality of U-shaped clips adapted to retain said first and second tubes within said first and second channel means, respectively, said clips each having a retaining projection at the end of each clip leg, each said retaining projection adapted to engage a predetermined one of the slots of said slot pairs.

19. A tubing cassette according to claim 17 further comprising:

a molded pressure line adapter means for transversely directing a lumen communicating pressure information to a pressure sensor, the adapter means comprising:

a hollow cylindrical body, open at one end and closed at the other, a transversely directed bore provided in the wall of the cylindrical body adjacent the closed end, said bore communicating with the interior of said body; and an annular channel formed in the external surface of said cylindrical body;

a pressure line adapter receiving means comprising:

an elongated aperture having a generally oblong cross-section, said aperture extending perpendicularly to said front and back surfaces;

a transverse rib fixed intermediate the open ends of said aperture and parallel to said front and back surfaces;

a first opening in said rib adapted to allow said pressure line adapter to pass therethrough;

a second opening in said rib, smaller than and in the same plane as said first opening, said second opening communicating with said first opening along a third opening smaller than said second opening;

a pressure conduit channel for receiving a pressure conduit and aligning it with said transversely directed bore, said channel transverse to said second opening, the axis of said channel intersecting the axis of said second opening;

whereby said pressure line adapter may be axially inserted into said first opening to align said annular channel with said rib, and moved laterally into alignment with said second opening.

20. A method of irrigating an endoscopic work site during an endoscopic surgical procedure comprising the steps of:

providing an irrigation pump means capable of pumping irrigating fluid at pressures suitable for any procedure selected from the group of laparoscopic, arthroscopic and hysteroscopic procedures;

providing a tubing set suitable for use in a chosen procedure selected from the group of laparoscopic, arthroscopic or hysteroscopic procedures;

providing said tubing set with a tubing cassette for maintaining predetermined portions of said tubing set in predetermined positions relative to each other;

coding said tubing cassette with a code to identify the procedure for which said tubing set is suitable;

providing decoding means on said pump means for reading said code on said tubing cassette and for adjusting said pump means to operate with characteristics identified by said code.

21. A method according to claim 20 further comprising the steps of:

providing a source of reduced pressure;

communicating said source of reduced pressure to said endoscopic work site via a flexible conduit made a part of said tubing set;

retaining said flexible conduit in said tubing cassette;

providing an aspiration regulating means;

coding said tubing cassette with a code to identify the aspiration characteristics for which said tubing set is suitable;

decoding said code and controlling said regulating means to operate with aspirating characteristics identified by said code.

* * * * *